United States Patent [19]

Oikawa et al.

[11] Patent Number: 5,894,084
[45] Date of Patent: Apr. 13, 1999

[54] PRESSURE CONTAINER

[75] Inventors: Yasuki Oikawa; Tsutomu Yamaguchi, both of Tsukuba, Japan

[73] Assignee: Agency of Industrial Science and Technology, Tokyo, Japan

[21] Appl. No.: 08/949,847

[22] Filed: Oct. 14, 1997

[30] Foreign Application Priority Data

Oct. 18, 1996 [JP] Japan .................. 8-276119

[51] Int. Cl.$^6$ .............. G01N 11/00; G01N 3/08; B65D 51/16
[52] U.S. Cl. .................. 73/37; 73/866; 73/859.6
[58] Field of Search .................. 73/37, 866, 859.6

[56] References Cited

U.S. PATENT DOCUMENTS

| | | | |
|---|---|---|---|
| 4,326,405 | 4/1982 | Ingle, Jr. | 73/37 |
| 4,513,603 | 4/1985 | Baillie | 73/37 |
| 4,805,443 | 2/1989 | Schroeder | 73/37 |
| 4,875,363 | 10/1989 | Hinduja et al. | 73/56 |
| 5,117,699 | 6/1992 | Johanson et al. | 73/866 |
| 5,119,681 | 6/1992 | Miszczak | 73/788 |
| 5,289,728 | 3/1994 | Johanson et al. | 73/866 |
| 5,348,694 | 9/1994 | Goldberger | 264/27 |
| 5,375,453 | 12/1994 | Rudd et al. | 73/37 |
| 5,668,305 | 9/1997 | Chi et al. | 73/37 |
| 5,677,477 | 10/1997 | Man et al. | 73/37 |

*Primary Examiner*—Hezron Williams
*Assistant Examiner*—J. David Wiggins
*Attorney, Agent, or Firm*—Oblon, Spivak, McClelland, Maier & Naustadt, P.C.

[57] ABSTRACT

A pressure container that easily fixes a sample or installs various measurement sensors onto a material tester before initiating various tests under an ambient pressure using the material tester, the container including a cover member that is mounted on the bottom surface of an upper loading frame plate with the loading cylinder of the material tester penetrating the center thereof, a bottom member that is mounted on the top surface of a lower loading frame plate with the platen of the material tester penetrating the center thereof, and a cylindrical side wall member having the same outer diameter as the cover member and the same inner diameter as the bottom member. The side wall member is disposed so as to slide vertically around the bottom member and can be detachably fixed to the cover member in its uppermost position in which the side wall member touches the cover member. This type of pressure container enables various preparatory work to be conducted without removing the loading frame plates from the material tester after a sample inside the pressure container has been adhered directly to the loading cylinder of the material tester.

2 Claims, 1 Drawing Sheet

PRESSURE CONTAINER

FIELD OF THE INVENTION

The present invention relates to a pressure container used in combination with a material tester during various tests under an ambient pressure using this material tester.

DESCRIPTION OF THE PRIOR ART

To conduct various tests under an ambient pressure using a material tester, pressure containers accommodating a material have commonly been used. Such pressure containers are robustly constructed to allow a predetermined pressure to be applied to samples. The material tester must have a very rigid loading frame so as to be loaded smoothly onto samples. Since upper and lower loading frame plates of the material tester must be precisely parallel to each other, considerable labor is required to remove and mount these plates. Thus, a sample is generally fixed in a pressure container, with the loading frame of the tester separated therefrom, before the pressure container is loaded on the loading section of the tester for tests. This method, however, cannot directly fit the sample to a loading cylinder of the tester, so the rigidity of the entire test system apparently decreases. This problem is more serious during tension tests that are significantly affected by the rigidity of the entire test system, wherein the tester cannot be easily loaded on a sample.

SUMMARY OF THE INVENTION

This invention is designed to resolve these problems, and its object is to provide a pressure container that easily fixes a sample or installs various measurement sensors onto a material tester before initiating various tests under an ambient pressure using the material tester.

To achieve this object, this invention provides a pressure container installed between the upper and lower loading frame plates of a material tester, comprising a cover member that is mounted on the bottom surface of the upper loading frame plate with a loading cylinder penetrating the center thereof, a bottom member that is mounted on the top surface of the lower loading frame plate with a lower platen penetrating the center thereof, and a cylindrical side wall member having an inner diameter equal to that of the bottom member, wherein the side wall member is disposed so as to slide vertically around the bottom member, and is detachably fixed to the cover member in its uppermost position, in which it touches the cover member; and the space surrounded by the cover, the bottom, and the side wall members can be sealed in a gas-tight manner.

The pressure container in this configuration according to this invention can be opened by sliding the side wall member downward. Thus, it enables tests to be conducted under a predetermined ambient pressure without removing loading frame plates from a material tester after various preparatory work has been conducted with a sample in the pressure container directly fixed to a loading cylinder of the material tester.

DESCRIPTION OF THE PREFERRED EMBODIMENT

Figure 1:
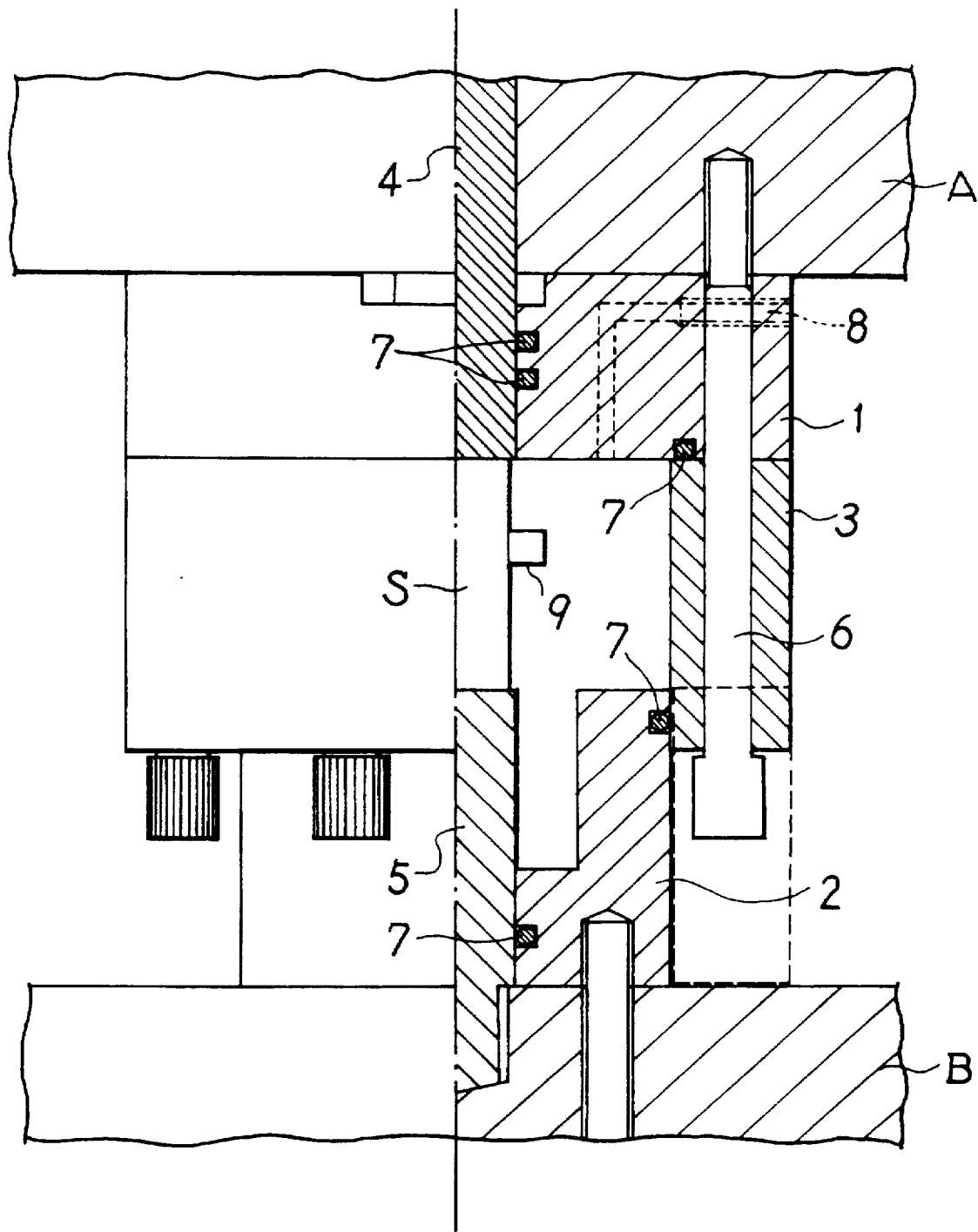
FIG. 1 is a schematic drawing showing in partial cross section a sample usage of a pressure container according to this invention.

An embodiment of this invention is described below with reference to the drawing.

FIG. 1 is a schematic drawing showing in partial cross section a sample usage of a pressure container according to this invention, and illustrates a sample set in the assembled pressure container.

As shown in FIG. 1, the pressure container is installed between an upper loading frame plate A and a lower loading frame plate B and comprises a cover member 1, a bottom member 2, and a side wall member 3, each having a circular external shape. The cover member 1 is mounted on the bottom surface of the upper loading frame plate A with a loading cylinder 4 penetrating the center thereof, and the bottom member 2 is mounted on the top surface of the lower loading frame plate B with a platen 5 penetrating the center thereof. The side wall member 3 is cylindrical and has the same outer diameter as the cover member 1 and the same inner diameter as the bottom member 2. The side wall member 3 is disposed so as to slide vertically around the bottom member 2 and is detachably fixed by a plurality of bolts 6 to the cover member 1 in its uppermost position in which it touches the cover member 1. An O ring 7 is installed between each of the members to provide gas-tight sealing. A pressure supply and discharge port 8 provided in the cover member 1 is used to apply a predetermined pressure to the inside of the pressure container during a material test.

In the FIGURE, reference number 9 is a sensor and the letter S indicates a sample.

Preparatory work is conducted as follows. The plurality of bolts 6 are first removed to remove the side wall 3 from the cover member, and the side wall is then moved to its lowermost position (indicated by the dotted line in the FIGURE) in order to open the inside of the pressure container. While the container is open, the sample S is placed in the container and then adhered to the loading cylinder 4 and the lower platen 5. The sensor 9 is mounted on the sample at the same time. The side wall member 3 is subsequently moved to its uppermost position and tightly connected to the cover member 1 using the bolts 6. The O rings 7 installed between the members then seal the inside of the pressure container so that a predetermined pressure can be applied to the inside of the pressure container through the pressure supply and discharge port 8. Forces pushing the cover member 1 upward and the bottom member 2 downward are held by the upper and the lower loading frame plates A and B, respectively.

Once the sample S has been set in the pressure container in this manner, the material tester is activated to move the loading cylinder 4 upward or downward for tension or compression tests.

This container enables various preparatory work to be conducted without removing the loading frame plates from the material tester after the side wall member has been slid downward to open the pressure container, followed by the direct connection of the sample in the container to the loading cylinder of the material tester. Therefore, this invention allows various tests, particularly, tension tests to be conducted easily under an ambient pressure without reducing the apparent rigidity of the loading frame of the material tester.

What is claimed is:

1. A pressure container installed between upper and lower loading frame plates of a material tester, comprising:
   a cover member with an inside and outside diameter that is mounted on the bottom surface of the upper loading frame plate with a loading cylinder penetrating the center thereof;
   a bottom member mounted on the top surface of the lower loading frame plate with a lower platen penetrating the center thereof, and a cylindrical side wall member with an inner diameter which is substantially equal to the outside diameter of the bottom member, wherein the side wall member is vertically slidable around the bottom member and is detachably fixed to the cover member in an uppermost position in which the side wall member contacts the cover member; and wherein a space surrounded by the cover, the bottom, and the side wall members is sealed in a gas-tight manner.

2. A pressure container according to claim 1 wherein the cover member has a pressure supply and discharge port for material tests.

* * * * *